US008853387B2

(12) United States Patent
Torri et al.

(10) Patent No.: US 8,853,387 B2
(45) Date of Patent: Oct. 7, 2014

(54) MIMETICS OF SULFATED OLIGOSACCHARIDES

(75) Inventors: Giangiacomo Torri, Milan (IT); Elena Vismara, Milan (IT); Israel Vlodavsky, Haifa (IL); Annamaria Naggi, Legnano (IT)

(73) Assignee: Istituto di Ricerche Chimiche e Biochimiche "G. Ronzoni", Milan (IT)

( * ) Notice: Subject to any disclaimer, the term of this patent is extended or adjusted under 35 U.S.C. 154(b) by 815 days.

(21) Appl. No.: 13/056,085

(22) PCT Filed: Jul. 9, 2009

(86) PCT No.: PCT/EP2009/058742
§ 371 (c)(1),
(2), (4) Date: Sep. 16, 2011

(87) PCT Pub. No.: WO2010/006982
PCT Pub. Date: Jan. 21, 2010

(65) Prior Publication Data
US 2012/0232263 A1    Sep. 13, 2012

(30) Foreign Application Priority Data

Jul. 15, 2008  (EP) .................................... 08160464

(51) Int. Cl.
*C07H 11/00* (2006.01)
*C07H 17/04* (2006.01)
*C07H 5/10* (2006.01)

(52) U.S. Cl.
CPC ................ *C07H 11/00* (2013.01); *C07H 17/04* (2013.01)
USPC .......................................................... 536/122

(58) Field of Classification Search
USPC .......................................................... 536/122
See application file for complete search history.

(56) References Cited

U.S. PATENT DOCUMENTS

| 5,739,115 | A | * | 4/1998 | Fugedi et al. ................... 514/24 |
| 6,143,730 | A |   | 11/2000 | Parish et al. |
| 2007/0185037 | A1 |   | 8/2007 | Ferro et al. |

FOREIGN PATENT DOCUMENTS

| WO | WO 96/09828 A | 4/1996 |
| WO | WO 2005/085264 A1 | 9/2005 |

OTHER PUBLICATIONS

Petitou et al, Bioorganic & Medicinal Chemistry, 1998, 6, 1509-16.*
Simizu et al, Cancer Science, 2004, 95, 553-58.*
Parrish et al, Cancer Research 1999, 59, 3433-41.*
Ilan et al., "Regulation, function and clinical significance of herparanase in cancer metastasis and angiogenesis", The International Journal of Biochemistry & Cell Biology, vol. 38, Issue 12, 2006, pp. 2018-2039.
Simizu et al., "Heparanase as a molecular target of cancer chemotherapy", Cancer Science, Jul. 2004, vol. 95, No. 7, pp. 553-558 (6 Pages).
Simizu et al., "Secretion of Heparanase Protein Is Regulated by Glycosylation in Human Tumor Cell Lines", The Journal of Biological Chemistry, vol. 279, No. 4, Issue of Jan. 23, pp. 2697-2703, 2004 (7 Pages).
Esko et al., "Molecular diversity of heparin sulfate", The Journal of Clinical Investigation, Jul. 2001, vol. 108, No. 2, pp. 169-171 (5 Pages).
Iozzo et al., "Heparan sulfate proteoglycans: heavy hitters in the angiogenesis arena", The Journal of Clinical Investigation, Aug. 2001, vol. 108, No. 3, pp. 349-355 (7 Pages).
Kirkpatrick et al., "Heparan sulfate proteoglycans at a glance", Journal of Cell Science, 2007, vol. 120, No. 11, pp. 1829-1832 (4 Pages).
Bishop et al., "Heparan sulphate proteoglycans fine-tune mammalian physiology", Nature, Apr. 26, 2007, vol. 446, No. 7139, pp. 1030-1037.
Vlodaysky et al., "Molecular properties and involvement of heparanase in cancer metastasis and angiogenesis", The Journal of Clinical Investigation, Aug. 2001, vol. 108, No. 3, pp. 341-347 (7 Pages).
Edovitsky et al., "Heparanase Gene Silencing, Tumor Invasiveness, Angiogenesis, and Metastasis", Journal of the National Cancer Institute, Aug. 18, 2004, vol. 96, No. 16, pp. 1219-1230 (12 Pages).
Shafat et al., "An ELISA method for the detection and quantification of human heparanase", Biochem. Biophys. Res. Commun., Mar. 24, 2006, vol. 341, No. 4, pp. 958-963 (12 Pages).
Sato et al., "Heparanase expression in human colorectal cancer and its relationship to tumor angiogenesis, hematogenous metastasis, and prognosis", Journal of Surgical Oncology, Sep. 15, 2004, vol. 87, Issue 4, pp. 174-181.
Yang et al., "The syndecan-1 heparan sulfate proteoglycan is a viable target for myeloma therapy", Blood, Sep. 15, 2007, vol. 110, No. 6, pp. 2041-2048 (9 Pages).
Hostettler, et al., "P-selectin- and heparanase-dependent antimetastatic activity of non-anticoagulant heparins", The FASEB Journal• Research Communication, 2007, 0892-6638/07/0021-3562, pp. 3562-3572 (11 Pages).
Borsig et al., "Heparin and cancer revisited: Mechanistic connections involving platelets, P-selectin, carcinoma mucins, and tumor metastasis", PNAS, Mar. 13, 2001, vol. 98, No. 6, pp. 3352-3357 (8 Pages).
Ludwig et al., "Endothelial P-Selectin as a Target of Heparin Action in Experimental Melanoma Lung Metastasis", Cancer Research, Apr. 15, 2004, vol. 64, pp. 2743-2750 (9 Pages).
Borsig et al., "Synergistic effects of L- and P-selectin in facilitating tumor metastasis can involve non-mucin ligands and implicate leukocytes as enhancers of metastasis", PNAS, Feb. 19, 2002, vol. 99, No. 4, pp. 2193-2198 (6 Pages).

(Continued)

*Primary Examiner* — Ganapathy Krishnan

(57) ABSTRACT

The present invention is directed to sulfated oligosaccharides having 4, 5 or 6 saccharidic units and wherein a glycosidic bond between two saccharide units is substituted by a C—C bond, and wherein the sulfation degree expressed as percentage of OH groups substituted by a $OSO_3^-$ group is comprised between 50 and 100%. The sulfated oligosaccharides according to the invention are useful as a drug, in particular in the treatment of angiogenesis, metastasis, and inflammation.

11 Claims, 5 Drawing Sheets

(56) References Cited

OTHER PUBLICATIONS

Guerrini et al., "Synthesis and characterisation of hexa- and tetrasaccharide mimics from acetobromomaltotriose and acetobromomaltose, and of C-disaccharide mimics from acetobromoglucose, obtained by electrochemical reduction on silver", Tetrahedron: Asymmetry, Jan. 10, 2005, vol. 16, Issue 1, pp. 243-253.

van den Bos et al., "Uronic Acids in Oligosaccharide Synthesis", European Journal of Organic Chemistry, Aug. 2007, vol. 2007, Issue 24, pp. 3963-3976.

Damager et al., Synthesis 2002, 3, 418-426.

Cottaz et al., "Chemoenzymatic approach to the preparation of regioselectively modified cyclodextrins. The substrate specificity of the enzyme cyclodextrin glucosyltransferase (CGTase)", J. Chem. Soc., Perkin Trans. 1, 1991, 2235-2241.

Classon et al., "New halogenation reagent systems useful for the mild one-step conversion of alcohols into iodides or bromides", J. Org. Chem., Dec. 1988, vol. 53, No. 26, pp. 6126-6130.

Takeo et al., "Synthesis of lycotetraose", Oct. 15, 1984, vol. 133, Issue 2, pp. 275-287.

Written Opinion for PCT/EP/2009/058742 dated Jan. 15, 2011.

Vlodaysky, et al., "Heparanase: Structure, Biological Functions, and Inhibition by Heparin-Derived Mimetics of Heparan Sulfate," Current Pharmaceutical Design, 2007, 13, pp. 2057-2073.

Vlodavsky, et al. "Heparanase: Structure, biological functions, and inhibition by heparin-derived mimetics of heparan sulfate", Current Pharmaceutical Design, 13(20): 2057-2073; 2007.

Guerrini, et al., "Synthesis and characterisation of hexa- and tetrasaccharide mimics from acetobromomaltotriose and acetobromomaltose, and C-disaccharide mims from acetobromoglucose, obtained by electrochemical reduction on silver", Tetrahedron Asymmetry, 16(1): 243-253; Jan. 10, 2005.

International Search Report and Written Opinion for PCT/EP2009/058742 dated Aug. 17, 2009.

\* cited by examiner

MIMETICS OF SULFATED OLIGOSACCHARIDES

This application is a national stage of PCT/EP2009/058742, filed on Jul. 9, 2009, which claims priority to EP Application No. 08160464.7, filed on Jul. 15, 2008, the entire contents and disclosures of which is hereby incorporated by reference.

In recent years there has been a growing interest towards the activity of oligosaccharides in the inhibition of metastasis and angiogenesis. In particular, it has been observed that non-coagulant species of heparin and various sulfated polysaccharides are active in the inhibition of heparanase.

Heparanase is an endoglycosidase involved in cleavage of heparan sulfate and hence in degradation and remodelling of the basement membrane and extracellular matrix (ECM). Heparanase activity facilitates cell invasion associated with cancer metastasis, angiogenesis, autoimmunity and inflammation.

Heparanase is up regulated in a variety of human tumours, including carcinomas of the colon, thyroid, liver, pancreas, bladder, cervix, ovary, breast, gastric, prostate, head and neck, salivary gland and nasopharynx, as well as multiple myeloma, leukaemia and lymphoma. In most cases, elevated levels of heparanase were detected in about 50% of the tumour specimens, with a higher incidence in pancreatic (78%) and gastric (80%) carcinomas, and in multiple myeloma (86%). In all cases, the normal looking tissue adjacent to the malignant lesion expressed little or no detectable levels of heparanase, suggesting that epithelial cells do not normally express the enzyme (*Regulation, function and clinical significance of heparanase in cancer metastatis and angiogenesis*; Ilan, Neta; Elkin, Michael; Volodaysly. The International Journal of Biochemistry & Cell Biology (2006), 38, 2018-2039. *Heparanase as a molecular target of cancer chemotherapy*; Simizu, Siro; Ishida, Keisuke; Osada, Hiroyuki. Cancer Science (2004), 95(7), 553-558. *Secretion of Heparanase Protein Is Regulated by Glycosylation in Human Tumor Cell Lines*; Simizu, Siro; Ishida, Keisuke; Wierzba, Michal K.; Osada, Hiroyuki. Journal of Biological Chemistry (2004), 279(4), 2697-2703).

Heparanase is an endoglycosidase involved in cleavage of heparan sulfate (HS), HS belongs to the family of highly sulfated and structurally heterogeneous polysaccharides, which are expressed as side-chains of proteoglycans (HSPG) i.e. syndecan, perlecan; on cell surfaces and in the extracellular matrix (ECM). Almost every type of animal cell has the capacity to synthesize HS that interacts with diverse ligands including growth factors/morphogens and their receptors, enzymes and enzyme inhibitors, cell-adhesion molecules, chemokines, various ECM proteins, and microbial proteins. HSPGs thus are essential for normal embryonic development, but are also implicated in homeostasis as well as in pathological processes, such as tumour metastasis. HSPG plays a key role in the self-assembly, insolubility and barrier properties of the ECM and tumour microenvironment. Cleavage of HS by heparanase therefore affects the integrity of tissues and hence has regulation effects on normal and pathological phenomena involving cell migration and response to changes in the ECM. In addition, HSPG interacts with VEGF, FGF-2, IL-8, which together direct the generation and maintenance of the tumour microenvironment. By cleaving HS chains of proteoglycans, heparanase releases HS-bound growth factors from the matrix along with proangiogenic fragments of HS. (*Molecular diversity of heparan sulphate*; Esko J., Lindahl U. J. Clin. Invest. (2001) 108, 169-171. *Heparan sulfate proteoglycans: Heavy hitters in the angiogenesis arena from molecular design to cellular function*. Iozzo, R. V., San Antonio, J. D. J. Clin. Invest. (2001)108, 349-355. *Heparan sulfate proteoglycans at a glance*; Kirkpatrick, Catherine A.; Selleck, Scott B. Journal of Cell Science (2007), 120(11), 1829-1832. *Heparan sulphate proteoglycans fine-tune mammalian physiology*; Bishop, Joseph R.; Schuksz, Manuela; Esko, Jeffrey D. Nature (2007), 446(7139), 1030-1037).

Mammalian heparanase over-expression is correlated with increased metastatic potential, tumour vascularity and poor postoperative survival of cancer patients. Heparanase activity facilitates cell invasion associated with cancer metastasis, angiogenesis, autoimmunity and inflammation. Heparanase can exert its role on tumour progression via both enzymatic and non-enzymatic mechanisms. In fact, the nonenzymatic form of protein can promote cell adhesion, cell survival, endothelial cell migration and invasion. In experimental animal models, over-expression of heparanase in tumour cells confers an invasive phenotype (*Molecular properties and function of heparanase in cancer metastasis and angiogenesis*; Vlodaysky, I., Friedmann, Y. J. Clin. Invest. (2001)108, 341-347), while heparanase gene silencing was demonstrated to markedly inhibit cancer metastasis and angiogenesis (*Heparanase gene silencing, tumor invasiveness, angiogenesis, and metastasis*: Edovitsky, E., Elkin, M., Zcharia, E., Peretz, T., and Vlodaysky, I. J Natl Cancer Inst, 2004, 96: 1219-1230. An ELISA method for the detection and quantification of human heparanase. Shafat, I., Zcharia, E., Nisman, B., Nadir, Y., Nakhoul, F., Vlodaysky, I., & Ilan, N. (2006). Biochem Biophys Res Commun 341, 958-963).

Cancer metastasis is a well-organized process; namely, benign neoplasms undergo a series of sequential but distinct changes to reach a malignant state. For example, a tumour can initially be benign and then become malignant through acquisition of mutations before proceeding all the way through the metastatic cascade. The mutations acquired lead to abnormal and uncontrolled proliferation.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

In order to metastasize, cells must first detach from the primary tumor, enter the vasculature or intravasate, circulate through the blood, attach to vessel walls, exit the vasculature or extravasate, and establish in a new surrounding, producing primary metastasis. This whole process is then repeated to give rise to secondary metastasis. The steps of angiogenesis, arrest and adhesion, and intravasation or extravasation involve subtle to extensive cell-surface degradation and remodeling of the ECM by various proteolytic enzymes secreted by the tumor cells.

Studies performed in our laboratory clearly indicate that heparanase is a most promising target for anti-cancer drug development. This statement was reinforced by clinical observations demonstrating a highly significant correlation between enhanced heparanase expression, metastatic potential, tumor vascularity and reduced postoperative survival of cancer patients. These observations, the anti-cancerous effect of heparanase-inhibiting strategies and the identification of a single functional heparanase gene and protein, indicate that the enzyme is a promising target for drug development (*Heparanase expression in human colorectal cancer and its relationship to tumor angiogenesis, hematogenous metastasis, and prognosis*: Sato, T., Yamaguchi, A., Goi, T., Hirono, Y., Takeuchi, K., Katayama, K., & Matsukawa, S. *J Surg Onco* (2004). 87, 174-181. *The syndecan*-1 *heparan sulfate*

*proteoglycan is a viable target for myeloma therapy*: Yang Yang, Veronica MacLeod, Yuemeng Dai, Yekaterina Khotskaya-Sample, Zachary Shriver, Ganesh Venkataraman, Ram Sasisekharan, Annamaria Naggi, Giangiacomo Torri, Benito Casu, Israel Vlodaysky, Larry J. Suva, Joshua Epstein, Shmuel Yaccoby, John D. Shaughnessy Jr, Bart Barlogie, and Ralph D. Sanderson Blood, 15 Sep. 2007, Volume 110, Number 6 2041-48).

Selectins are vascular cell adhesion molecules promoting initial leukocyte-endothelial interactions. In addition, P- and L-selectin are implicated in pathological processes involving inflammation, reperfusion injury, and cancer. We and others have reported that heparin attenuated metastasis in mouse models of carcinomas and melanomas, primarily through inhibition of selectin interactions (*P-selectin-and heparanase-dependent antimetastatic activity of non-anticoagulant heparins*: Nina Hostettler, Annamaria Naggi, Giangiacomo Torri, Riva Ishai-Michaeli Benito Casu, Israel Vlodaysky, and Lubor Borsig The FASEB Journal•Research Communication 2007, 0892-6638/07. *Heparin and cancer revisited: mechanistic connections involving platelets, P-selectin, carcinoma mucins, and tumor metastasis*: Borsig, L., Wong, R., Feramisco, J., Nadeau, D. R., Varki, N. M., and Varki, A. (2001) Proc. Natl. Acad. Sci. U.S.A. 98, 3352-3357. *Endothelial P-selectin as a target of heparin action in experimental melanoma lung metastasis*: Ludwig, R. J., Boehme, B., Podda, M., Henschler, R., Jager, E., Tandi, C., Boehncke, W. H., Zollner, T. M., Kaufmann, R., and Gille, J. Cancer Res. (2004) 64, 2743-2750). Synergistic effects of L- and P-selectin in facilitating tumor metastasis can involve non-mucin ligands and implicate leukocytes as enhancers of metastasis (*Synergistic effects of L- and P-selectin in facilitating tumor metastasis can involve non-mucin ligands and implicate leukocytes as enhancers of metastasis*: Borsig, L., Wong, R., Hynes, R. O., Varki, N. M., and Varki, A. (2002) Proc. Natl. Acad. Sci. U.S.A. 99, 2193-2198).

Several attempts were made in the past to find compounds which are mimetics of natural compounds such as heparin, and that can effectively act in the inhibition of heparanase.

U.S. Pat. No. 6,143,730 discloses that maltohexaose sulphate is very active in inhibiting vascularization of tumoral cells and angiogenesis. However, the synthesis of maltohexaose sulphate is very complex and expensive, making the use of this compound on a large scale difficult. Phosphomannopentaose sulphate (PI-88) is also indicated as an active compound for angiogenesis inhibition and antimetastatic. (WO2005085264 and US20070185037).

The present invention is directed towards new sulfated oligosaccharides, preferably comprising 4, 5 or 6 saccharide units and wherein two saccharide units are bond through a hydrolize resistant C—C bond and wherein the sulfation degree expressed as percentage of OH groups substituted by a $OSO_3^-$ group is comprised between 50 and 100%.

Preferably, the C—C bond connects either the $2^{nd}$ and $3^{rd}$ saccharide unit, or the $3^{rd}$ and $4^{th}$ unit. The C involved in the C—C bond between the two saccharide units, can be any available C atom, i.e. the carbon atom in position 1, 5 or 6. Furthermore, the configuration of the C—C bond, when the carbon is in the 1 position, can be either α or β.

In a preferred embodiment of the invention, the oligosaccharides according to the invention, malto-oligosaccharides (MOS), are represented by the following formulas:

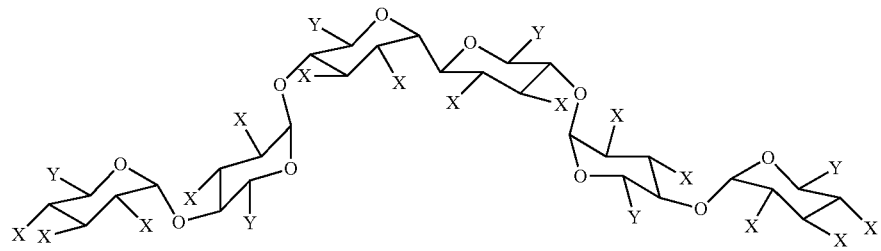

αβ

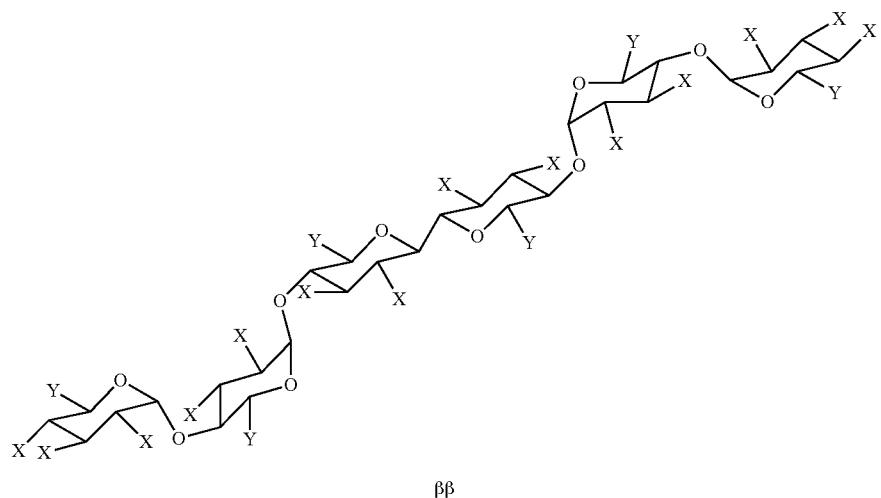

ββ

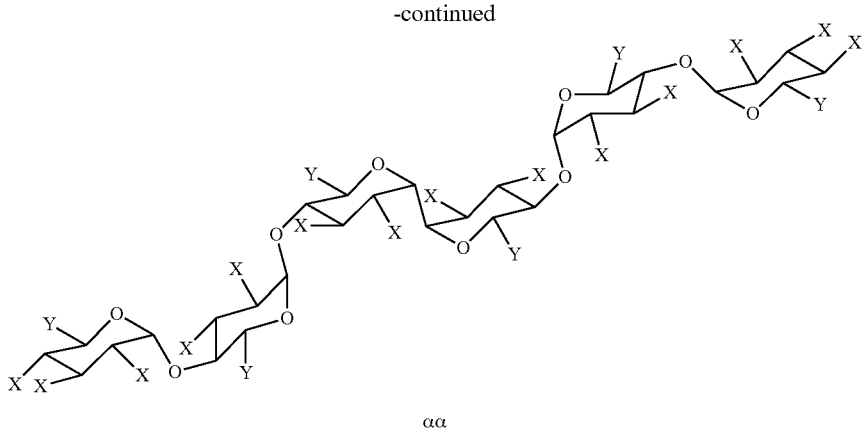

αα

Wherein X can be OH or $OSO_3^-$ or an optionally sulfated (oligo)saccharide group; Y is selected from the group consisting of $CH_2OH$, $CH_2OSO_3^-$, COOH, COOR wherein R is selected from the group consisting of alkyl, aryl, acyl, aroyl, alkyl sulfonyl, aryl sulfonyl, PEG or a PEG derivative.

In another preferred embodiment of the invention the oligosaccharides according to the invention are the 5-5 isomers represented by the following formulas:

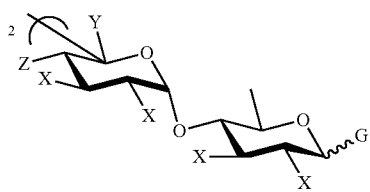

5,5

Wherein Y and X have the above defined meanings; G is OH, $OSO_3^-$, OR wherein R is selected from the group consisting of alkyl, aryl, acyl, aroyl, alkyl sulfonyl, aryl sulfonyl, PEG, a PEG derivative or an optionally sulfated (oligo)saccharide group; Z is OH, $OSO_3^-$ or an optionally sulfated (oligo)saccharide group.

In a further embodiment of the invention the oligosaccharides according to the invention are the 6-6 isomers represented by the following formula:

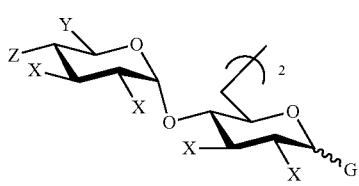

6,6

Wherein Y, X, G and Z have the above defined meanings.

In a preferred embodiment of the invention, the oligosaccharides according to the invention are useful in the treatment of angiogenesis.

In another embodiment of the invention, the oligosaccharides according to the invention are useful as antimetastatic compounds.

Preferably, the oligosaccharides according to the invention, when used as anti-metastatic and/or anti-angiogenetic drug, have a sulphation degree of from 60 to 100% in terms of percentage of groups X which are $OSO_3^-$.

In a preferred embodiment of the invention, it is disclosed the use of the oligosaccharides according to the invention as an anti-inflammatory drug. Preferably, the oligosaccharides according to the invention, when used as anti-inflammatory drug, have a sulphation degree of from 80 to 100% in terms of percentage of groups X which are $OSO_3^-$.

The oligosaccharides according to the present invention can be prepared starting from the corresponding compound wherein X═OH. The methodology is known from the prior art (*Synthesis and characterization of hexa- and tetrasaccharide mimics from acetobromomaltotriose and acetobromomaltose, and of C-disaccharide mimics from acetobromoglucose, obtained by electrochemical reduction of silver*: M. Guerrini, S. Guglieri, R. Santarsiero and E. Vismara: Tetrahedron: *Asymmetry* 16 (2005) 243-253).

Although the publication only discloses the synthesis of tetra- and hexasaccharides by dimerization of di- and trisaccharides, it is evident that by using a mixture of di- and trisaccharide it is obtained a mixture of tetra-penta- and hexasaccharides.

Starting form the obtained tetra-penta- and hexasaccharides, it is possible to increase the number of saccharide units by using conventional glycosylation methods.

Before sulfation, the neutral oligosaccharide precursors can be electro-oxidized to uronic acids with 2,2,6,6-tetramethylpiperidine-1-oxyl as mediator. This strategy allows uronic acid residues incorporation into the new sulfated oligosaccharides and their further esterification (*Uronic acid in oligosaccharide synthesis*: van den Bos, Leendert J.; Codee, Jeroen D. C.; Litjens, Remy E. J. N.; Dinkelaar, Jasper; Overkleeft, Herman S.; van der Marel, Gijsbert A. European Journal of Organic Chemistry (2007), (24), 3963-3976).

The tests performed on 1,1 α,β sulfated hexasaccharide (S67) demonstrate that the activity of this compound towards selectins inhibition is close to the activity of heparin. It is well known that heparin is very active towards selectins inhibition but cannot be used as an anti-inflammatory compound as such because of its anticoagulant properties. Thus, the result obtained in the test represents an excellent result since the oligosaccharides according to the invention do not present anticoagulant activity.

MATERIALS

Figure 1:
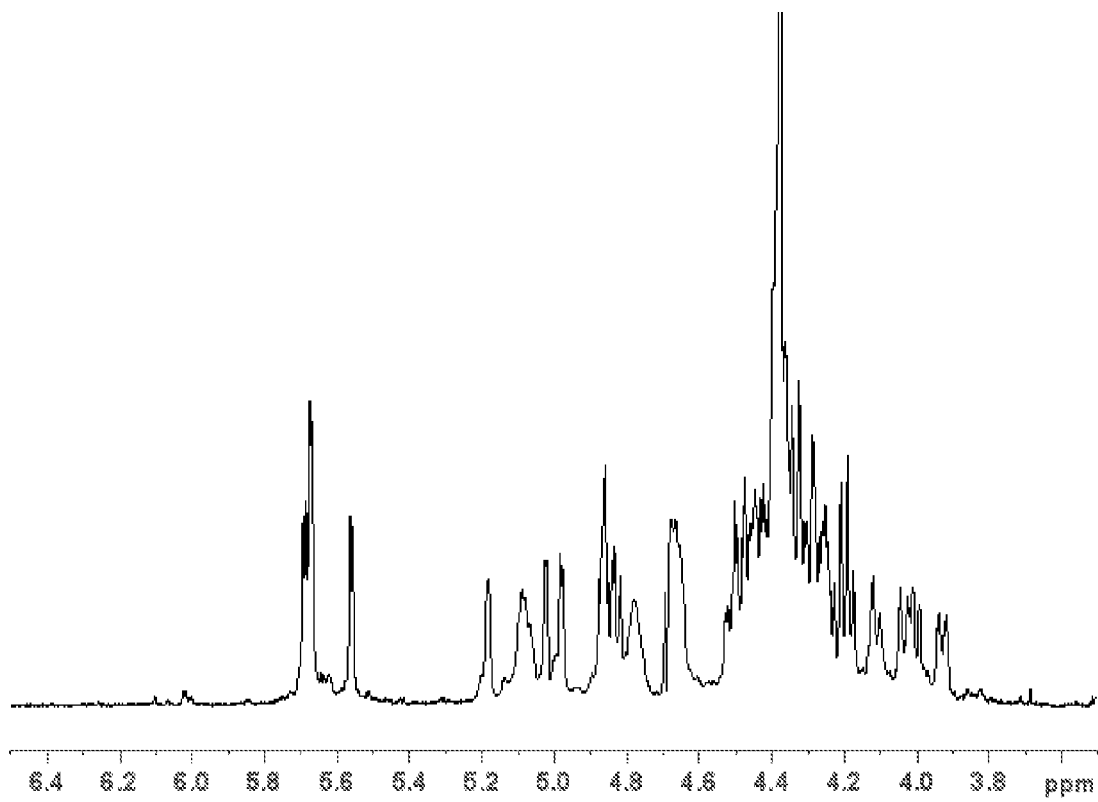
FIG. 1 shows the monodimensional $^1H$ NMR spectrum of S67.
Figure 2:
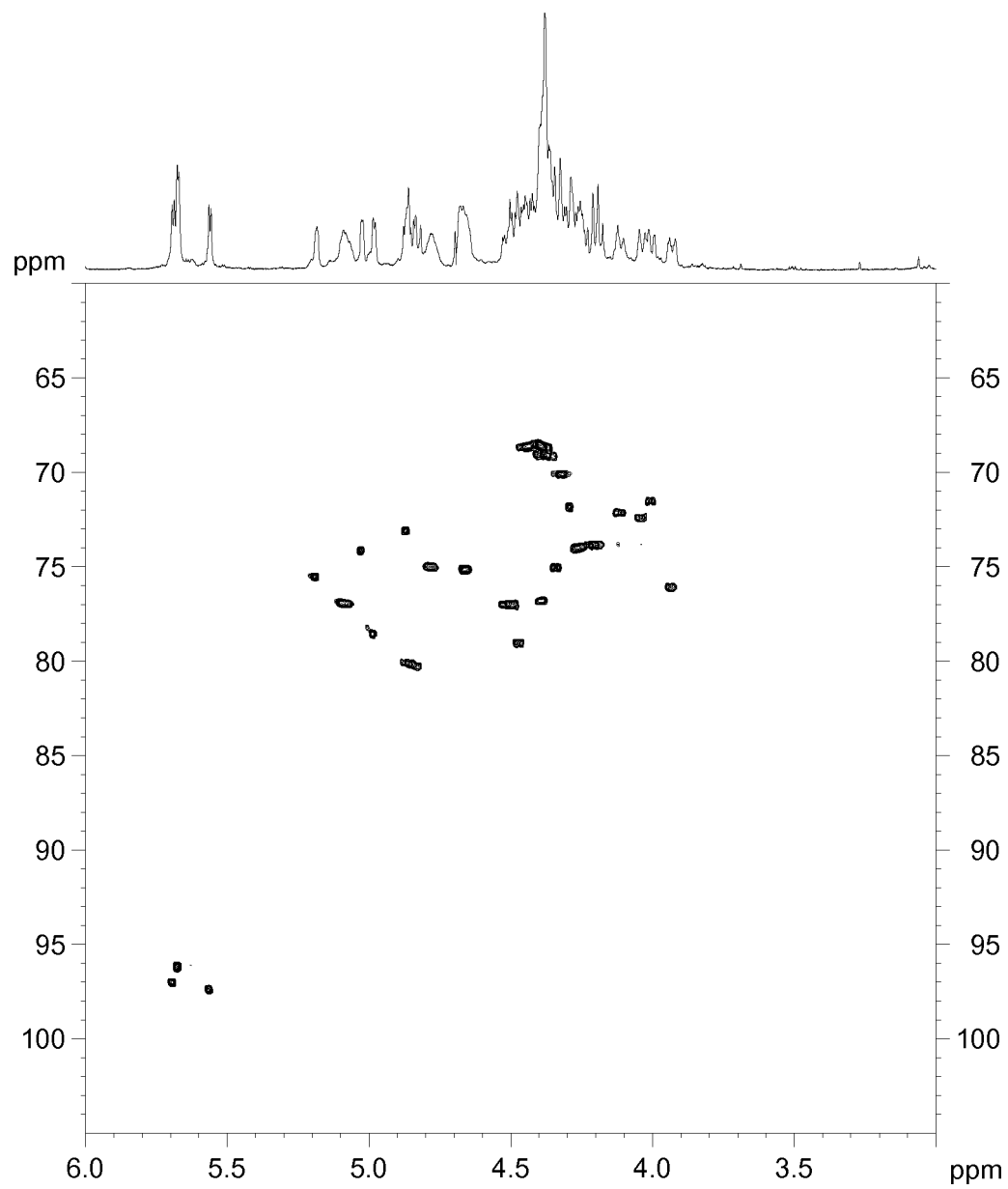
FIG. 2 shows the bidimensional spectrum $^1H$-$^{13}C$ NMR of S67
Figure 3:
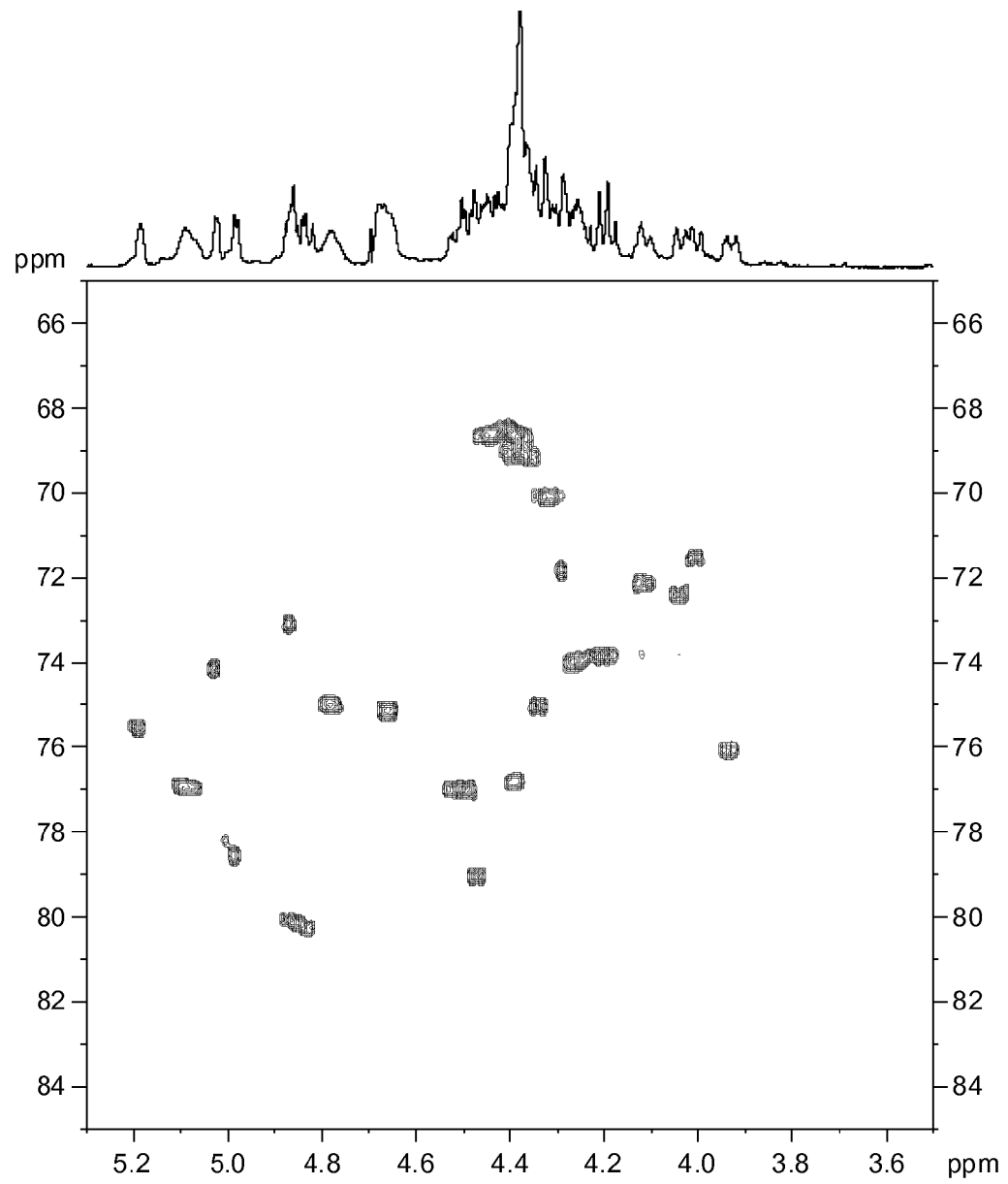
FIG. 3 shows a detail of the bidimensional spectrum $^1H$-$^{13}C$ NMR of S67.

Maltohexaose sulfate (MHS) was prepared by sulfation of commercial maltohexaose according to the general sulfation procedure.

Acetobromomaltose (ABM) and acetobromomaltotriose (ABMT) were prepared from commercial maltose monohydrate and maltotriose (Damager, I.; Olsen, C. E.; Moller, B. L.; Motawia, M. S. *Synthesis* 2002, 3, 418-426).

Acetobromomaltose (ABM) and acetobromomaltotriose (ABMT) are also the starting compounds of peracetylated 6-CH$_2$-iodo reducing-end maltose (IRM) and peracetylated 6-CH$_2$-iodo reducing-end maltotriose (IRMT), respectively. They were converted into the corresponding peracetylated 1,6-anydromaltose and 1,6-anydromaltotriose, precursor respectively of the peracetilated 6-formyl-maltose and 6-formyl-maltotriose (Cottaz, S.; Apparu, C.; Driguez, H. *J. Chem. Soc. Perkin Trans* 1 1991, 2235-2241). Iodination of the peracetilated 6-hydroxyl-maltose and 6-hydroxyl-maltotriose, coming from the formyl group hydrolysis, respectively afforded IRM and IRMT (Classon, B.; Liu, Z.; Samuelsson, B. *J. Org. Chem.* 1988, 53, 6126-6130).

Maltose is the starting compound of peracetylated 6-CH$_2$-iodo non reducing-end maltose (INRM). It was first protected as 4',6' benzylidene maltose and then fully acetylated. Debenzylation has given peracetylated 4',6'-hydroxyl maltose, which has been protected in 6' with the trityl group, and acetylated in 4' (Takeo, K.; Shinmitsu, K. *Carbohydr. Res.* 1984, 133, 135-145). After detritylation, 6' hydroxyl peracetylated maltose has been iodinated to INRM (Classon, B.; Liu, Z.; Samuelsson, B. *J. Org. Chem.* 1988, 53, 6126-6130).

The degree of sulfation of the final derivatives was determined through bi-dimensional NMR technique (i.e. HSQC). In the case of homogeneous O-sulfation, the HSQC NMR spectrum appears with typical low field shifts of carbon and hydrogen signals respect to that of the corresponding unsulfated compounds.

In the case of incomplete and non homogeneous derivatization an arbitrary evaluation of the spectra was done. Two different areas (in the case of α,β hexasaccharide derivatives $A_S$: $^{13}C$ 81-72/$^1H$ 5.3-4.28 ppm; $A_{nS}$: $^{13}C$ 77-71/$^1H$ 4.28-3.90 ppm) for sulfated and unsulfated secondary carbon were identified, while for primary alcohols a direct evaluation of sulfate residue can be done at $^{13}C$ 70-68/$^1H$ 4.55-4.3 ppm. ($A_{6S}$) respect to $^{13}C$ 62-60/$^1H$ 4.0-3.8 ppm. ($A_{6OH}$).

In a totally sulfated hexasaccharide mimic compound the area of O-sulfated secondary carbons ($A_s$) is the 65% of the total ($A_S+A_{nS}$). In a case of under-sulfation, the degree of sulfation is measured as follow:

$$[A_S/(A_S+A_{nS})\times 0.65]+A_{6S}/(A_{6S}+A_{6OH})=\text{Degree of sulfation}$$

General Synthetic Procedures
Step 1—Synthesis of Acetylated Neutral Precursors by Preparative Electrolysis Experiments.

Peracetylated halosugars silver cathode potentiostatic electroreductions, redox potential between −1.3 V and −1.7 V on the bases of each halosugar cyclic voltammetry, were exhaustively run in anhydrous acetonitrile, in the presence of a quaternary organic ammonium salt as supporting electrolyte. After the work-up of the reaction mixture, dimers have been isolated by flash chromatography on silica gel. Big efforts have been dedicated to their purification. For this purpose, HPLC semi preparative column was successfully used.

Step 2—Deacetylation. In agreement of the Conventional Methodology.
Step 3—Sulfation.

The Sulfated derivatives according to the present invention are obtained by conventional sulfation methods of the deacetylated derivatives. By changing the reaction condition it is possible to obtain the desired sulfation degree.

EXAMPLE 1

From Acetobromaltose (ABM) to 1,1 Tetrasaccharides 1 (α,α), 2 (α,β)

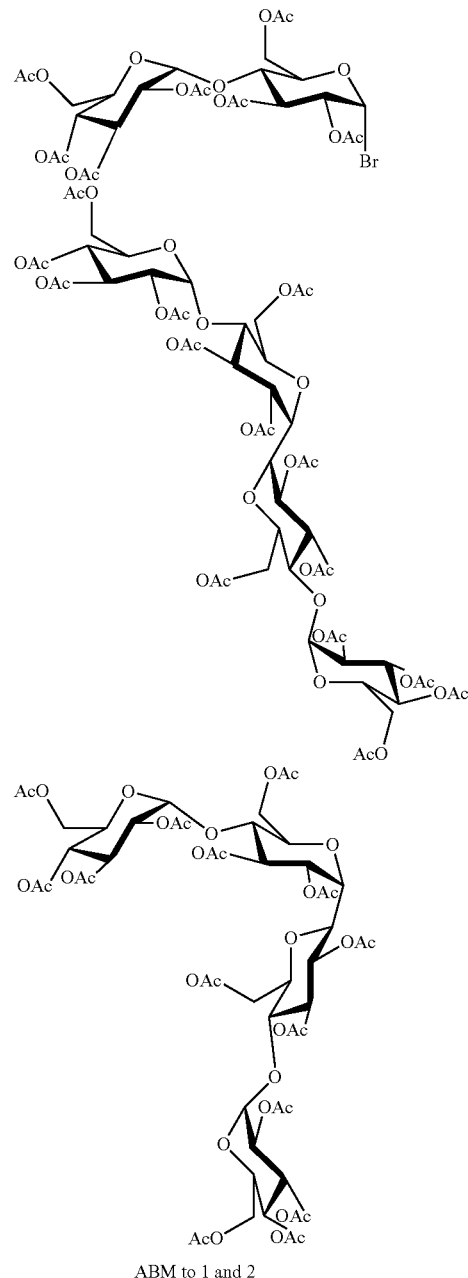

ABM to 1 and 2

The electrolysis was carried out under potentiostatic conditions at room temperature under nitrogen atmosphere in a 2-compartment cell, divided with an anion-exchange membrane. 50 mL of cathode solution made by anhydrous acetonitrile and containing 1.15 g of tetraethylammonium perchlorate (TeaP) as supporting electrolyte were pre-electrolysed 10 minutes between −1.0 and −1.9 V, using a silver plate as cathode and a silver plate as anode in 50 mL of anhydrous acetonitrile saturated with tetraethylammonium bromide. An anionic ion exchange membrane (Sybron Chemicals) was used to separate anode and cathode compartments. After the pre-eletrolysis, 4.11 g (5.89 mmol) of ABM were added to the cathode solution and were exhaustively electrolysed at −1.600V. The solution at the cathode compartment was concentrated and precipitated with AcOEt. The solid supporting electrolyte was filtered off. The filtrate was evaporated at reduced pressure and the residue was flash-chromatographed on silica gel from 3:7 hexane/acetate to acetate, isolating 1α,α and 2α,β, overall yields 40%.

EXAMPLE 2

From Acetobromomaltotriose (ABMT) to 1,1 Hexasaccharides 3 (α,α), 4 (α,β) and 5 (β,β)

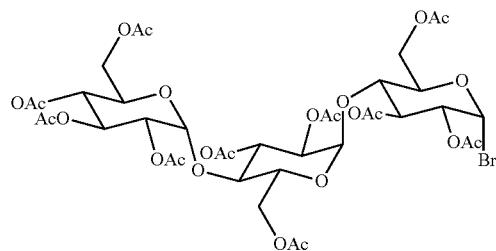

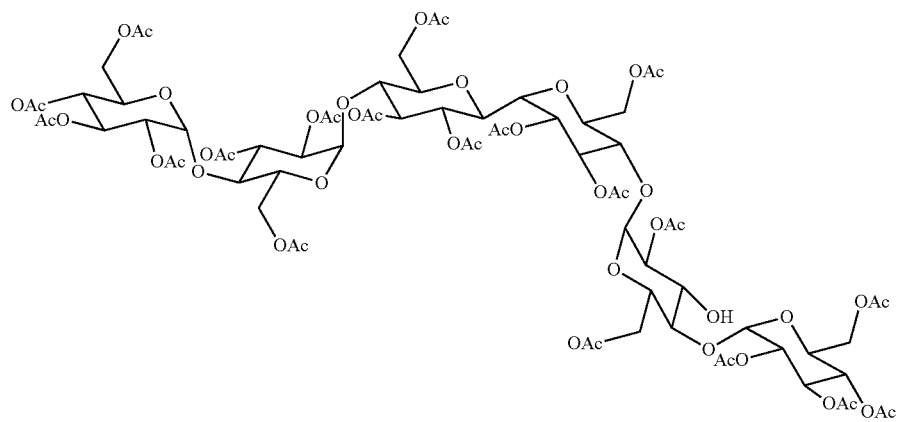

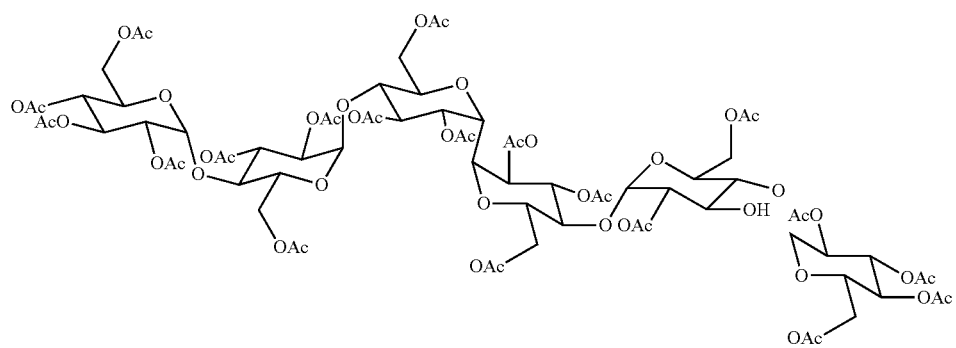

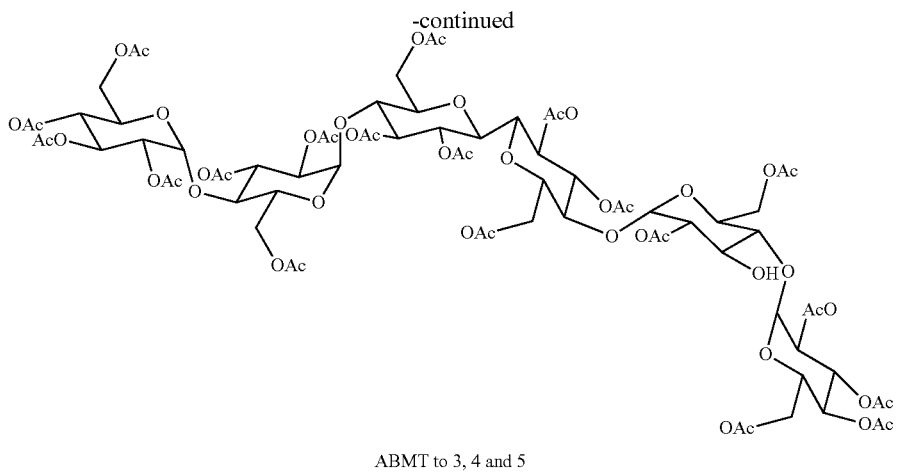

ABMT to 3, 4 and 5

The electrolysis was carried out under potentiostatic conditions at room temperature under nitrogen atmosphere in a 2-compartment cell, divided with an anionic ion exchange membrane (Sybron Chemicals) 50 mL of cathode solution made by anhydrous acetonitrile and containing 1.15 g of tetraethylammonium perchlorate (TeaP) as supporting electrolyte were pre-electrolysed 10 minutes between −1.0 and −1.9 V, using a silver plate as cathode and a silver plate as anode in 50 mL of anhydrous acetonitrile saturated with tetraethylammonium bromide. The Sybron™ membrane was used to separate anodic and cathode compartments. After the pre-eletrolysis, 5.82 g (5.89 mmol) of ABMT were added to the cathode solution and were exhaustively electrolysed at −1.600V. The solution at the cathode compartment was concentrated and precipitated with AcOEt. The solid supporting electrolyte was filtered off. The filtrate was evaporated at reduced pressure and the residue was flash-chromatographed on silica gel from 4:6 hexane/acetate to acetate, obtaining a crude mixture of α,α, α,β and β,β isomers (34% yields). After a further flash-chromatography of the crude mixture, fractions enriched in single isomer were obtained. These fractions were purified through semi preparative HPLC yielding pure isomers of 3,4 and 5. Semi-preparative HPLC was performed on a Hypersil BDS C18 250×10 mm column from Thermo Hypersil, a Rheodine valve of 10 µL and a flow rate of 5 ml/min. Samples were dissolved in ACN at the concentration of 100 mg/ml; 70 µL were injected.

EXAMPLE 3

From CH$_2$I-reducing-End Maltose (IRM) to 5,5 Tetrasaccharide 6 and 6,6 Reducing-End Tetrasaccharide 7

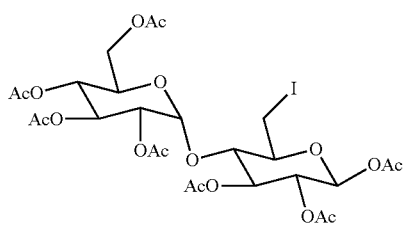

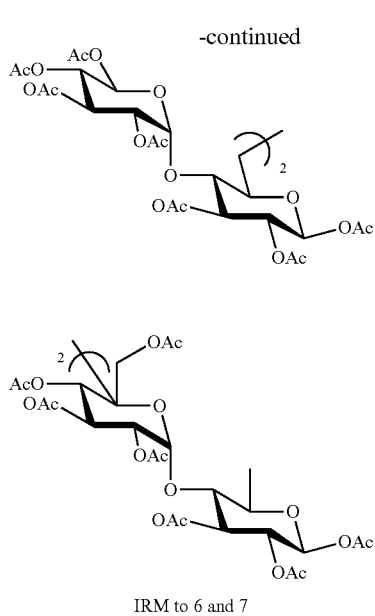

IRM to 6 and 7

A solution of 217 mg of tetraethylammonium tetrafluoborate in 10 ml of anhydrous acetonitrile was extensively degassed with N$_2$ and pre-electrolysed briefly at −1.3000V at the cathode of a two compartment electrolytic cell until the obtainment of a low and constant current intensity. A silver plate was used both as cathode and a as anode, the latter being immersed in 8 mL of a 0.1M solution of tetraethylammonium tetrafluoborate in anhydrous acetonitrile. A porous glass septum was used to separate anodic and cathode compartments. After the pre-electrolysis, 186 mg (0.25 mmol) of IRM were added to the cathode solution and were exhaustively electrolysed under N$_2$ at −1.3000V. The solution at the cathode compartment was concentrated and precipitated with AcOEt. The solid supporting electrolyte was filtered off. The filtrate was evaporated at reduced pressure and the residue was flash-chromatographed on silica gel (3:7 hexane/acetate). Dimerization of IRM afforded ca. 48% of tetrasaccharides (73% of 6 and 27% of 7)

EXAMPLE 4

From CH₂I-Non Reducing-End Maltose (INRM) to 6,6 Non Reducing-End Tetrasaccharide 8

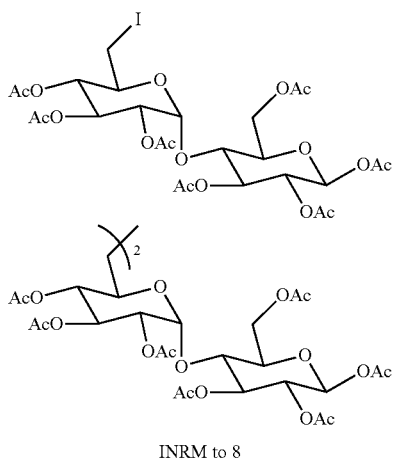

INRM to 8

A solution of 217 mg of tetraethylammonium tetrafluoborate in 10 ml of anhydrous acetonitrile was extensively degassed with $N_2$ and pre-electrolysed briefly at −1.3000V at the cathode of a two compartment electrolytic cell until the obtainment of a low and constant current intensity. A silver plate was used both as cathode and a as anode, the latter being immersed in 8 mL of a 0.1M solution of tetraethylammonium tetrafluoborate in anhydrous acetonitrile. A porous glass septum was used to separate anodic and cathode compartments. After the pre-electrolysis, 186 mg (0.25 mmol) of INRM were added to the cathode solution and were exhaustively electrolysed under $N_2$ at −1.3000V. The solution at the cathode compartment was concentrated and precipitated with AcOEt. The solid supporting electrolyte was filtered off. The filtrate was evaporated at reduced pressure and the residue was flash-chromatographed on silica gel (3:7 hexane/acetate). INRM afforded 8 in ca. 60% yield.

EXAMPLE 5

From CH₂I-Reducing-End Maltotriose (IRMT) to 5,5 Hexasaccharide 9 and 6,6 Reducing-End Hexasaccharide 10

A solution of 217 mg of tetraethylammonium tetrafluoborate in 10 ml of anhydrous acetonitrile was extensively degassed with $N_2$ and pre-electrolysed briefly at −1.3000V at the cathode of a two compartment electrolytic cell until the obtainment of a low and constant current intensity. A silver plate was used both as cathode and a as anode, the latter being immersed in 8 mL of a 0.1M solution of tetraethylammonium tetrafluoborate in anhydrous acetonitrile. A porous glass septum was used to separate anodic and cathode compartments. After the pre-electrolysis, 240 mg (0.25 mmol) of IRMT were added to the cathode solution and were exhaustively electrolysed under $N_2$ at −1.3000V. The solution at the cathode compartment was concentrated and precipitated with AcOEt. The filtrate was evaporated at reduced pressure and the residue was flash-chromatographed on silica gel (3:7 hexane/acetate). A mixture of 9 and 10 was further purified through semi preparative HPLC, yielding pure isomers of 9 and 10. Semi preparative HPLC was performed on a Hypersil BDS C18 250×10 mm column from Thermo Hypersil, a Rheodine valve of 100 μL and a flow rate of 5 ml/min. Samples were dissolved in ACN at the concentration of 100 mg/ml; 704 were injected. IRMT afforded ca 31% of hexasaccharides (60% of 9 and 40% of 10).

Sulfation of Mimetic Oligosaccharides

EXAMPLE 6

From 1,1 Hexasaccharides 3 (α,α), 4 (α,β) and α,α/α,β/β,β Diastereoisomer Mixtures to the Corresponding Sulfated Derivatives Step 1—Deacetylation 0.266 mmol of the above derivatives and 22 ml of 0.2 M MeONa (4.47 mmol, 1.2 eq./eq.OAc) in MeOH were stirred overnight at r.t, in a vessel equipped with a $CaCl_2$ trap to avoid moisture. An equal volume of water was added and pH was adjusted to 7 with Amberlite™ IR-120 ($H^+$ form). The resin was filtered off and solvent was removed obtaining neutral dimer as a white solid in quantitative yield.

Step 2—Sulfation—Table 1

590 mg of sulfur trioxide pyridine complex (3.68 mmol, 10 eq per eq —OH) were added to a pyridine solution of deacetylated dimer (0.0185 mmol, $4×10^{-3}$ M). The reaction mixture was warmed up to 80° C. and stirred for 6 hrs, avoiding moisture with a $CaCl_2$ trap. The mixture cooled down to room temperature, was neutralized with a saturated solution of $NaHCO_3$ and exhaustively evaporated under vacuum. The solid residue was water dissolved and chromatographed on TSK column.

TABLE 1

Example Samples Identification and Sulfation Degree

| Sample | Diastereoisomer (%) | Sulfation degree (%) |
|---|---|---|
| Ex. 2 P3314 | α,α 80%, 20% α,β | >90 |
| Ex. 2 P3377 | α,β > 95 | ~60 |
| Ex. 2 P3609 | α,α:β,β:αβ 25:25:50 | >90 |
| Ex. 2 P3677 | α,β > 95 | >90 |
| Ex. 2 S67 | α,β~100 | ~100 |

Biological Activities—Experimental Methods and Results
Heparanase Activity.

Sulfated compound was tested at two concentrations (1 & 5 μg/ml) for its ability to inhibit the heparanase enzyme, using metabolically sulfate labeled ECM as a substrate. Briefly, sulfate labeled ECM coating the surface of 35-mm tissue culture dishes, is incubated (37° C., pH 6.0, 4 h, 1 ml final volume) with recombinant human heparanase (10 ng/ml) in the absence and presence of increasing amounts of each compound. The reaction mixture contains: 50 mM NaCl, 1 mM DTT, 1 mM $CaCl_2$, and 10 mM buffer Phosphate-Citrate, pH 6.0. To evaluate the occurrence of proteoglycan degradation, the incubation medium is collected and applied for gel filtration on Sepharose 6B columns (0.9×30 cm). Fractions (0.2 ml) are eluted with PBS at a flow rate of 5 ml/h and counted for radioactivity. The excluded volume ($V_O$) is marked by blue dextran and the total included volume ($V_t$) by phenol red. Degradation fragments of HS side chains are eluted at 0.5<Kav<0.8 (peak II). Results are best presented as the actual gel filtration profiles. Numerical values derived from these graphs are presented in FIG. 1 as heparanase activity (% of control), where: Heparanase activity=Kav×total cpm in peak II (fractions 15-35). Kav=(Ve−Vo/Vt−Vo).
Control Kay=Kay obtained in the presence of enzyme alone (without inhibitors).
Effect of Sulfated Malto-Oligosaccharides Mimics (MOS) on Hpa Activity—Tables 1 and 2.

TABLE 2

Sample Identification, Sulfation Degree and Hpa Activity

| Sample | Diast. (%) | Sulf. degree (%) | Heparanase activity (5 μg/ml) |
|---|---|---|---|
| Ex. 2 P3314 | α,α 80% α,β 20% | >90 | 39 |
| Ex. 2 P3377 | α,β > 95 | ~60 | 65 |
| Ex. 2 P3609 | α,α: β,β: αβ 25:25:50 | >90 | 55 |
| Ex. 2 P3677 | α,β > 95 | >90 | 12 |
| MHS | — | >80 | 27 |
| control | — | — | 100 |

Experimental Metastasis. Table 1 and FIG. 4

Compounds are tested for inhibition of B16-BL6 lung colonization. For this purpose, C57BL6 mice (n=5 mice per group) receive a single i.p injection of 0.2 ml PBS (control) or 0.2 ml PBS containing 250 μg of each compound, 20 min prior to i.v inoculation of B16-BL6 melanoma cells (1×10$^5$ cells/mouse). Mice are sacrificed 15 days later, lungs are fixed and examined for the number of melanoma colonies on the lung surface.

Figure 4:
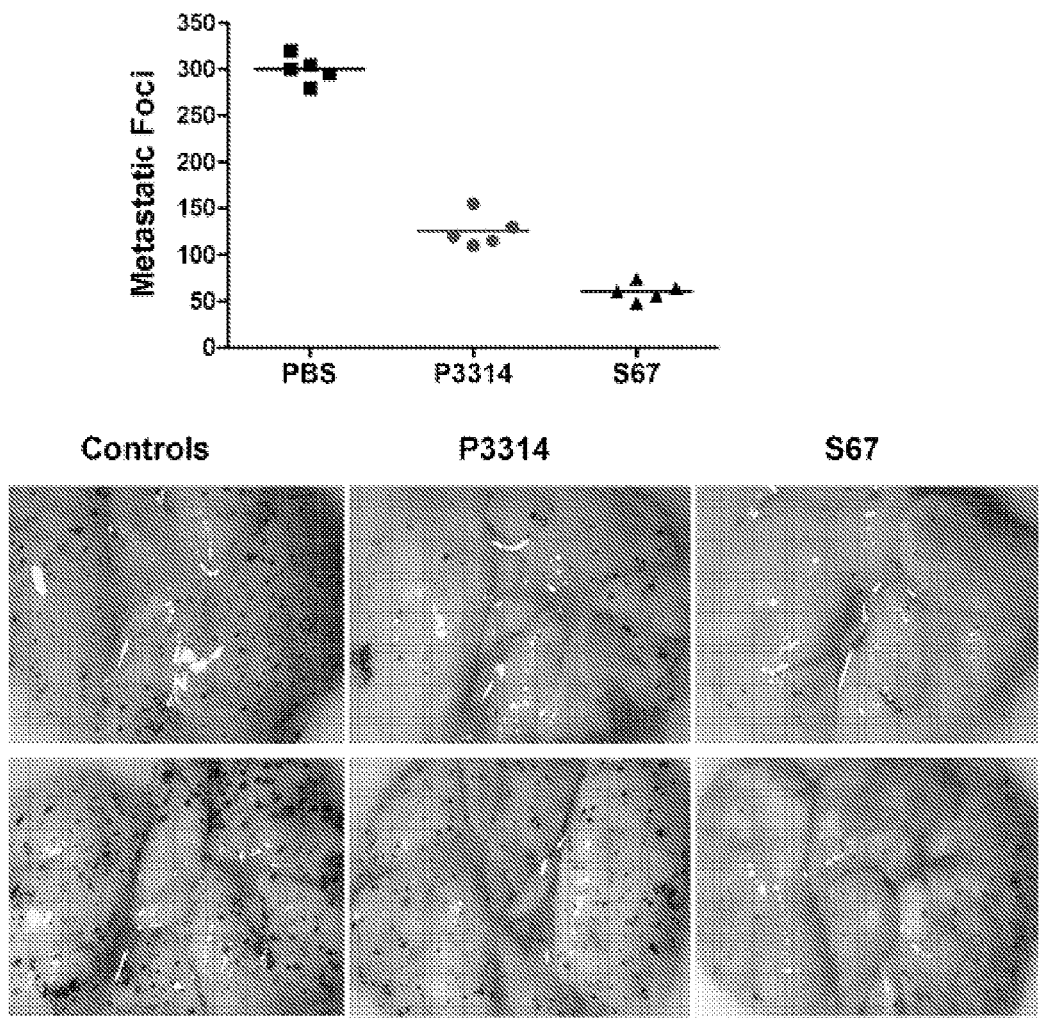
FIG. 4 shows the activity of S67 and P3314 in the reduction of metastatic foci of B16BL6 melanoma.

In FIG. 4 mice were injected with 250 μg of S67 10 prior to B16BL6 melanoma injection (300000 cells). The experiment with P3314 reported in FIG. 4 was conducted using an amount of 150 μg instead of 250 μg. The test with P3314 was repeated with 250 μg and the average number of metastatic foci was 75.

Figure 5:
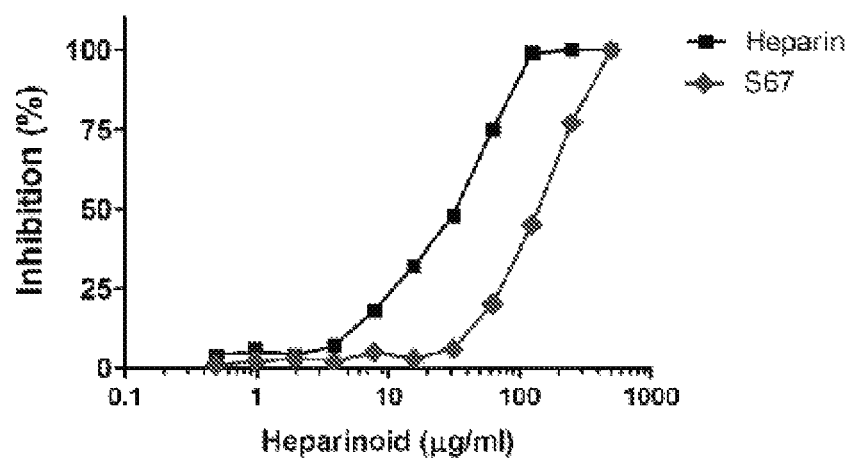
FIG. 5 shows the activity of S67 in selectins inhibition.

Selectin Activity—FIG. 5

The P-selectin inhibitory potential was measured by inhibitory ELISA using LS180 cells, heparin (UFH) as a control. The results are reported in FIG. 5.

The invention claimed is:

1. Sulfated oligosaccharides wherein a glycosidic bond between two saccharide units is substituted by a C—C bond, wherein the C—C bond is between the positions 1-1, 2-2, 5-5 or 6-6, and wherein the sulfation degree, expressed as percentage of OH groups substituted by a $OSO_3^-$ group, is between 50 and 100%.

2. Sulfated oligosaccharides according to claim 1 wherein the oligosaccharide has 4, 5 or 6 saccharide units.

3. Sulfated oligosaccharides according to claim 2 wherein the bond is between the positions 1,1 and the conformation is α-α, α-β or β-β.

4. Sulfated oligosaccharides according to claim 1, wherein the compound is expressed by the formula:

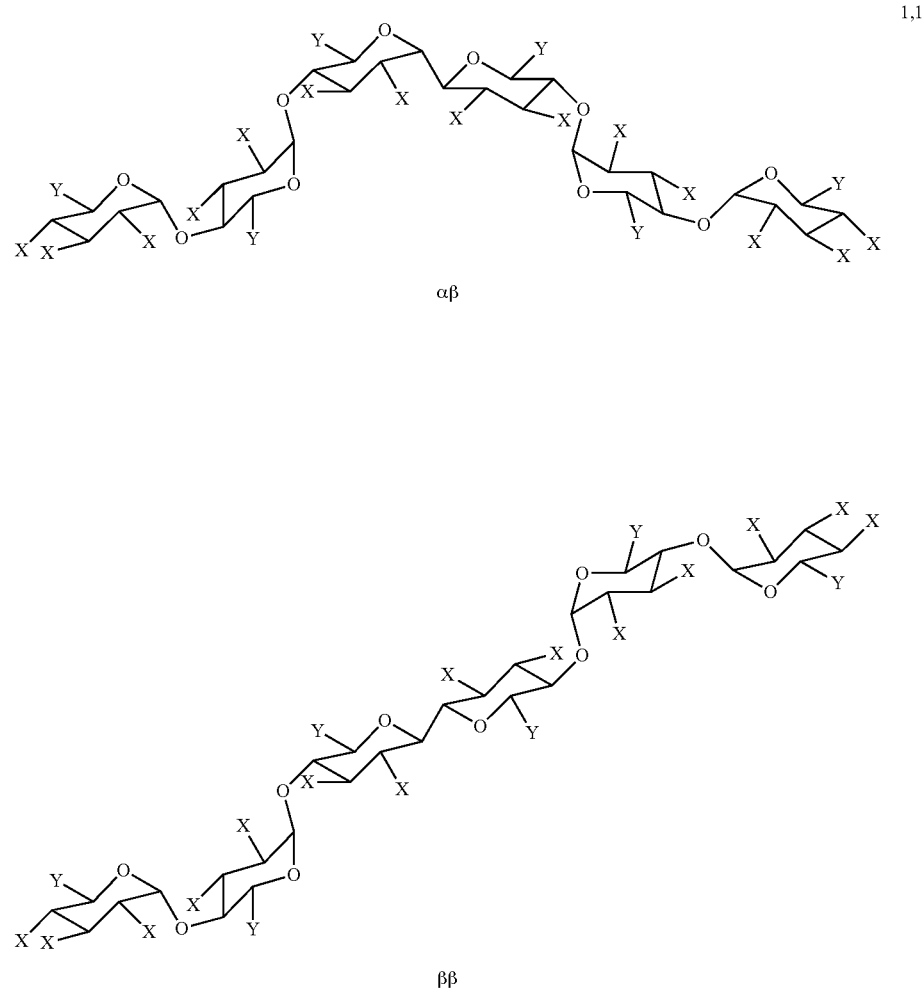

-continued

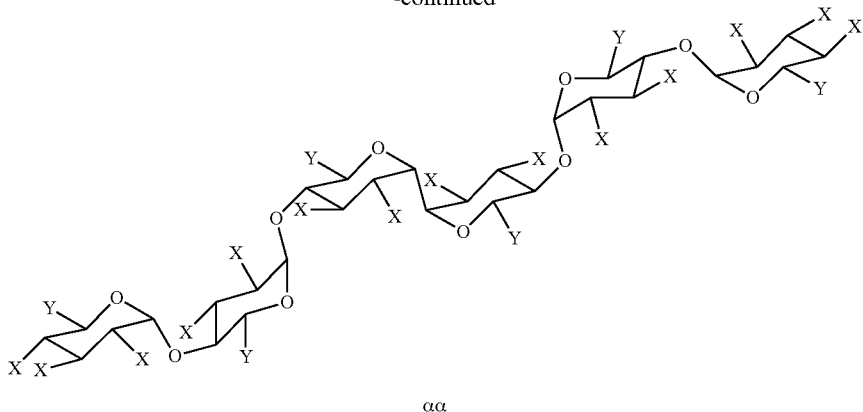

αα wherein X can be OH, $OSO_3^-$ or an optionally sulfated saccharide or oligosaccharide group; Y is selected from the group consisting of $CH_2OH$, $CH_2OSO_3^-$, COOH, COOR wherein R is selected from the group consisting of alkyl, aryl, acyl, aroyl, alkyl sulfonyl, aryl sulfonyl, PEG.

5. Sulfated oligosaccharides according to claim 1, wherein the compound is expressed by the formula:

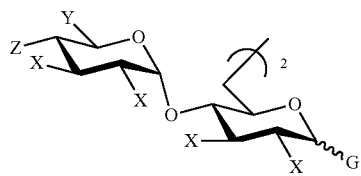

wherein X can be OH, $OSO_3^-$ or an optionally sulfated saccharide or oligosaccharide group; Y is selected from the group consisting of $CH_2OH$, $CH_2OSO_3^-$, COOH, COOR wherein R is selected from the group consisting of alkyl, aryl, acyl, aroyl, alkyl sulfonyl, aryl sulfonyl, PEG; G is OH, $OSO_3^-$, OR wherein R is selected from the group consisting of alkyl, aryl, acyl, aroyl, alkyl sulfonyl, aryl sulfonyl, PEG, or an optionally sulfated saccharide or oligosaccharide group; Z is OH, $OSO_3^-$ or an optionally sulfated saccharide or oligosaccharide group.

6. Sulfated oligosaccharides according to claim 1 wherein the oligosaccharide is an hexasaccharide and the C—C bond is between the third and fourth unit.

7. A method of treatment of angiogenesis comprising administering to a mammalian in need of such treatment an effective amount of a compound of claim 1.

8. A method of treatment of metastasis comprising administering to a mammalian in need of such treatment an effective amount of a compound of claim 1.

9. The method of claim 7 wherein the compound has a sulfation degree between 60 and 100%.

10. A method of treatment of inflammation comprising administering to a mammalian in need of such treatment an effective amount of a compound of claim 1.

11. The method of claim 10 wherein the compound has a sulfation degree between 80 and 100%.

* * * * *